(12) United States Patent
Den Boef et al.

(10) Patent No.: US 7,656,518 B2
(45) Date of Patent: Feb. 2, 2010

(54) METHOD OF MEASURING ASYMMETRY IN A SCATTEROMETER, A METHOD OF MEASURING AN OVERLAY ERROR IN A SUBSTRATE AND A METROLOGY APPARATUS

(75) Inventors: Arie Jeffrey Den Boef, Waalre (NL); Karel Diederick Van Der Mast, Helmond (NL); Maurits Van Der Schaar, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 241 days.

(21) Appl. No.: 11/729,962

(22) Filed: Mar. 30, 2007

(65) Prior Publication Data

US 2008/0239318 A1    Oct. 2, 2008

(51) Int. Cl.
*G01N 21/00* (2006.01)

(52) U.S. Cl. .................................................. 356/237.2

(58) Field of Classification Search ................. 356/401, 356/601, 237.2
See application file for complete search history.

(56) References Cited

U.S. PATENT DOCUMENTS

| | | | |
|---|---|---|---|
| 4,938,600 A | 7/1990 | Into ............................ | 356/401 |
| 5,280,437 A | 1/1994 | Corliss ....................... | 364/559 |
| 5,703,692 A | 12/1997 | McNeil et al. .............. | 356/445 |
| 5,880,838 A | 3/1999 | Marx et al. ................. | 356/351 |
| 5,963,329 A | 10/1999 | Conrad et al. .............. | 356/372 |
| 6,538,740 B1 | 3/2003 | Shiraishi et al. ............ | 356/401 |
| 6,608,690 B2 | 8/2003 | Niu et al. .................... | 356/635 |
| 6,699,624 B2 | 3/2004 | Niu et al. ....................... | 430/5 |
| 6,704,661 B1 | 3/2004 | Opsal et al. ..................... | 702/27 |
| 6,721,691 B2 | 4/2004 | Bao et al. .................... | 702/189 |
| 6,738,138 B2 | 5/2004 | Wei ............................. | 356/369 |
| 6,753,961 B1 | 6/2004 | Norton et al. ............... | 356/364 |
| 6,768,542 B2 * | 7/2004 | Ise et al. ................... | 356/237.2 |
| 6,768,983 B1 | 7/2004 | Jakatdar et al. ............... | 706/46 |
| 6,772,084 B2 | 8/2004 | Bischoff et al. ............. | 702/127 |
| 6,785,638 B2 | 8/2004 | Niu et al. .................... | 702/189 |
| 6,813,034 B2 | 11/2004 | Rosencwaig et al. ........ | 356/601 |
| 6,819,426 B2 | 11/2004 | Sezginer et al. ............. | 356/401 |
| 6,856,408 B2 | 2/2005 | Raymond .................... | 356/601 |
| 6,861,660 B2 * | 3/2005 | Almogy et al. ........ | 250/559.45 |
| 6,919,964 B2 | 7/2005 | Chu ............................ | 356/601 |
| 6,928,628 B2 | 8/2005 | Seligson et al. ................. | 716/4 |
| 6,954,267 B2 * | 10/2005 | Abraham et al. .......... | 356/237.2 |
| 6,972,852 B2 | 12/2005 | Opsal et al. ................. | 356/625 |
| 6,974,962 B2 | 12/2005 | Brill et al. ................... | 250/548 |
| 6,987,572 B2 | 1/2006 | Lakkapragada et al. ..... | 356/601 |
| 7,046,376 B2 | 5/2006 | Sezginer ..................... | 356/601 |

(Continued)

FOREIGN PATENT DOCUMENTS

EP        1 628 164 A2    2/2006

(Continued)

*Primary Examiner*—Tarifur R. Chowdhury
*Assistant Examiner*—Isiaka O Akanbi
(74) *Attorney, Agent, or Firm*—Sterne, Kessler, Goldstein & Fox P.L.L.C.

(57) ABSTRACT

In a method of measuring asymmetry in a scatterometer, a target portion is illuminated twice, first with 0° of substrate rotation and secondly with 180° of substrate rotation. One of those images is rotated and then that rotated image is subtracted from the other image. In this way, asymmetry of the scatterometer can be corrected.

11 Claims, 5 Drawing Sheets

U.S. PATENT DOCUMENTS

| | | |
|---|---|---|
| 7,061,615 B1 | 6/2006 | Lowe-Webb ................. 356/401 |
| 7,061,623 B2 | 6/2006 | Davidson ..................... 356/497 |
| 7,061,627 B2 | 6/2006 | Opsal et al. .................. 356/601 |
| 7,068,363 B2 | 6/2006 | Bevis et al. ............... 356/237.5 |
| 2002/0041374 A1* | 4/2002 | Ohshima et al. .......... 356/237.2 |
| 2003/0025895 A1 | 2/2003 | Binnard ........................ 355/72 |
| 2004/0119970 A1 | 6/2004 | Dusa et al. ................ 356/237.1 |
| 2006/0033921 A1 | 2/2006 | Den Boef et al. ............ 356/446 |
| 2006/0066855 A1 | 3/2006 | Boef et al. ................... 356/401 |
| 2006/0126074 A1 | 6/2006 | Van Der Werf et al. ...... 356/489 |
| 2006/0139592 A1 | 6/2006 | Den Boef et al. .............. 355/53 |

FOREIGN PATENT DOCUMENTS

| | | |
|---|---|---|
| EP | 1 628 164 A3 | 4/2006 |
| KR | 2003053690 A | 7/2003 |
| KR | 2004070676 A | 8/2004 |
| KR | 10-2006-0108437 | 10/2006 |

* cited by examiner

METHOD OF MEASURING ASYMMETRY IN A SCATTEROMETER, A METHOD OF MEASURING AN OVERLAY ERROR IN A SUBSTRATE AND A METROLOGY APPARATUS

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Asymmetry in the scatterometer (which shows up as tool induced shift (TIS)) as well as errors in determining the center of the pupil plane can cause difficulties in measuring overlay errors.

SUMMARY

It is desirable to provide a method and apparatus in which TIS and/or errors in determining the center of the pupil plane is/are compensated for or reduced. Preferably this is done without any large increase in throughput time.

According to an embodiment of the invention, there is provided a method of measuring asymmetry in a scatterometer, the method including: first illumination of a target pattern with radiation and measuring a first two-dimensional angular scatter spectrum of radiation reflected and/or scattered by the target pattern by using the scatterometer to measure intensity at a plurality of pre-determined angular positions relative to the target pattern; relatively rotating the target pattern and the scatterometer by about 180° in a plane substantially perpendicular to the optical axis of the scatterometer; second illumination of the target pattern with radiation and measuring a two-dimensional angular scatter spectrum by using the scatterometer to measure intensity at the plurality of pre-determined portions relative to the target pattern and rotating that angular scatter spectrum by about 180° to produce a second two-dimensional angular scatter spectrum; and producing a sensor correction value for each of the plurality of pre-determined angular positions by, for each of the plurality of pre-determined positions, subtracting the intensity at the respective pre-determined position of the first two-dimensional angular scatter spectrum from the intensity at the respective pre-determined position of the second two-dimensional angular scatter spectrum.

According to an embodiment of the invention, there is provided method of measuring asymmetry in a scatterometer due to illumination beam asymmetry, the method including: first measurement using a detector of the scatterometer of the intensity of radiation of an illumination beam at a plurality of pre-determined positions relative to the detector in the cross-section of the illumination beam to produce a first map of intensities; relatively rotating the illumination beam and the scatterometer by about 180° in a plane substantially perpendicular to the axis of the illumination beam; second measurement using the detector of the intensity of radiation of the illumination beam at the plurality of pre-determined positions relative to the detector and rotating the thereby produced map of intensities by 180° to produce a second map of intensities; and producing an illumination asymmetry correction value for each of the plurality of pre-determined positions by, for each of the plurality of pre-determined positions, subtracting the intensity at the respective pre-determined position of the first map of intensities from the intensity at the respective pre-determined position of the second map of intensities.

According to an embodiment of the invention, there is provided a metrology apparatus configured to measure a property of a substrate, the apparatus including: a radiation projector configured to illuminate a target portion of a substrate with radiation; a detector configured to measure an intensity of reflected and/or scattered radiation from the target portion at a plurality of pre-determined angular positions relative to the target portion; a system configured to relatively rotate the target portion and the scatterometer by about 180° in a plane substantially perpendicular to the target portion; and a controller adapted to control illumination of the target pattern with radiation and determine a first two-dimensional angular scatter spectrum of radiation reflected and/or scattered by the target pattern by using the detector to measure intensity at a plurality of pre-determined angular positions relative to the target pattern, relatively rotate the target pattern and the scatterometer by about 180° in a plane substantially perpendicular to the optical axis of the scatterometer, then control illumination of the target pattern with radiation and measuring a two-dimensional angular scatter spectrum by using the detector to determine intensity at the plurality of pre-determined portions relative to the target pattern and rotate that angular scatter spectrum by about 180° to produce a second two-dimensional angular scatter spectrum, and produce a sensor correction value for each of the plurality of pre-determined angular positions by, for each of the plurality of pre-determined positions, subtracting the intensity at the respective pre-determined position of the first two-dimensional angular scatter spectrum from the intensity at the respective pre-determined position of the second two-dimensional angular scatter spectrum.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1A:
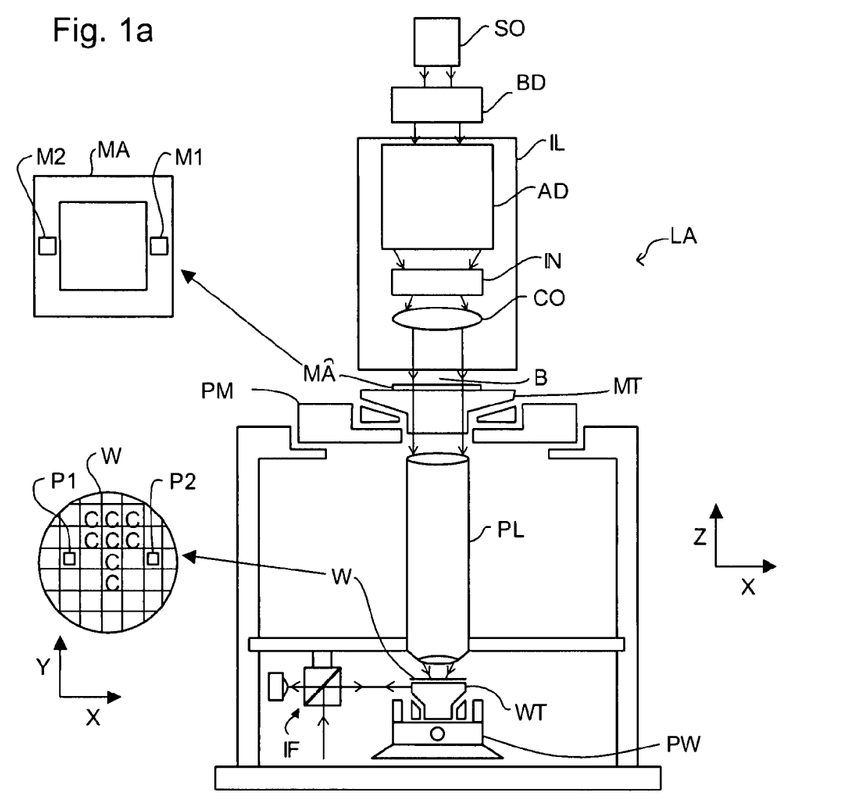
FIG. 1a depicts a lithographic apparatus in accordance with an embodiment of the invention.

FIG. 1a schematically depicts a lithographic apparatus LA. The apparatus includes an illumination system (illuminator) IL configured to condition a radiation beam B (e.g. UV radiation or EUV radiation); a support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device (e.g. mask) MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1a) can be used to accurately position the patterning device (e.g. mask) MA with respect to the path of the radiation beam B, e.g. after mechanical retrieval from a mask library, or during a scan. In general, movement of the support structure (e.g. mask table or pattern support) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure (e.g. mask table) MT may be connected to a short-stroke actuator only, or may be fixed. Patterning device (e.g. mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g. mask) MA, the mask alignment marks may be located between the dies.

The depicted apparatus could be used in at least one of the following modes:

1. In step mode, the support structure (e.g. mask table) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure (e.g. mask table) MT and the substrate table WT are scanned synchronously while a pattern imparted to the radiation beam is projected onto a target portion C (i.e. a single dynamic exposure). The velocity and direction of the substrate table WT relative to the support structure (e.g. mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
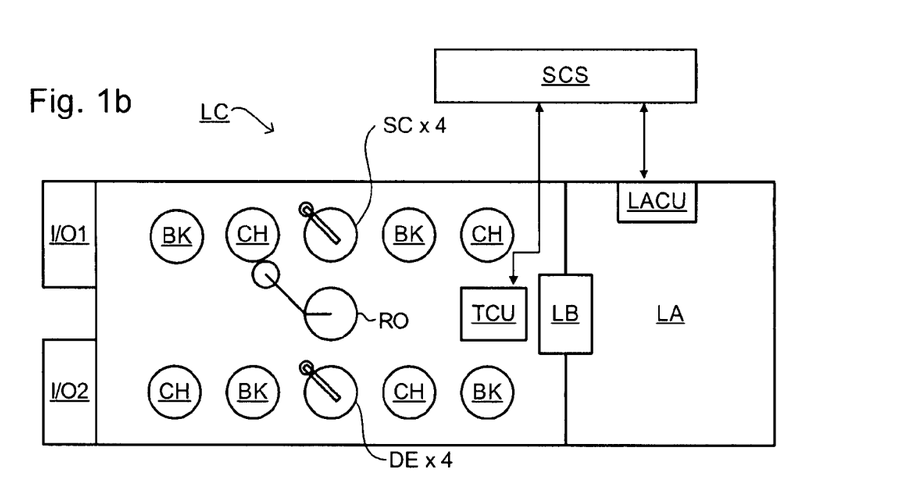
FIG. 1b depicts a lithographic cell or cluster in accordance with an embodiment of the invention.

As shown in FIG. 1b, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 2:
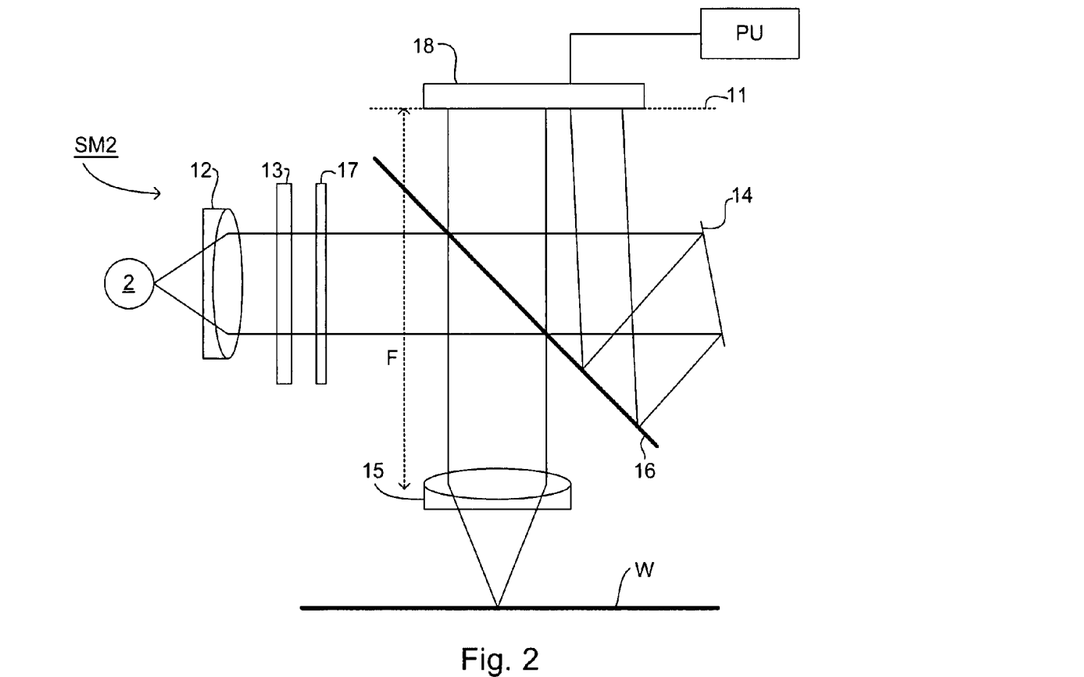
FIG. 2 depicts a scatterometer in accordance with an embodiment of the invention.

FIG. 2 depicts a scatterometer SM2 which may be used in accordance with an embodiment of the present invention. In this device, the radiation emitted by radiation source 2 is focused using lens system 12 through interference filter 13 and polarizer 17, reflected by partially reflective surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length F of the lens system 15. However the pupil plane may instead be re-imaged with auxiliary optics (not shown) onto the detector. The pupil plane is the plane in which the radial position of radiation defines the angle of incidence and the angular position defines azimuth angle of the radiation. The detector is a two-dimensional detector so that a two-dimensional angular scatter spectrum of the substrate target can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, about 405-790 nm or even lower, such as about 200-300 nm. The interference filter may be tunable rather than including a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$ and a spacing of at least 2 $\delta\lambda$ (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

In an embodiment of the present invention, steps are taken to account for a asymmetry in the overlay (scatterometry) sensor of FIG. 2 which would otherwise show up as tool induced shift (TIS).

One way of solving this assymetry is to illuminate the target pattern (which may be based on a diffractive pattern; i.e. a grating) with radiation and measuring at the detector 18 the intensity, at a plurality of pre-determined positions 100 (i.e. at each of the pixels of the detector) in a two dimensional array, of the reflected and/or scattered radiation (usually integrated over time).

The target portion is then rotated (i.e. either the substrate or the sensor or both are rotated) by about 180° in the plane of the substrate (or in a plane substantially perpendicular to the optical axis of the microscope objective lens 15 of the scatterometer) and the measurement is made again.

The apparatus of FIG. 2 may include a controller configured to rotate the target portion. The rotation of the target portion or the substrate may be done with a conventional system, e.g. a motor. The controller may further be configured to control illumination of the target pattern with radiation and to determine a spectrum of radiation (e.g. a two-dimensional angular scatter spectrum). In addition, the controller may also be adapted to output correction values as will be explained in more details below.

Tool induced shift (TIS) (which could be errors in the determination of the center of the pupil plane, for example) can then be eliminated in the following way: first one of the measured images is rotated through about 180°. This is illustrated schematically in FIG. 3.

Figure 3:
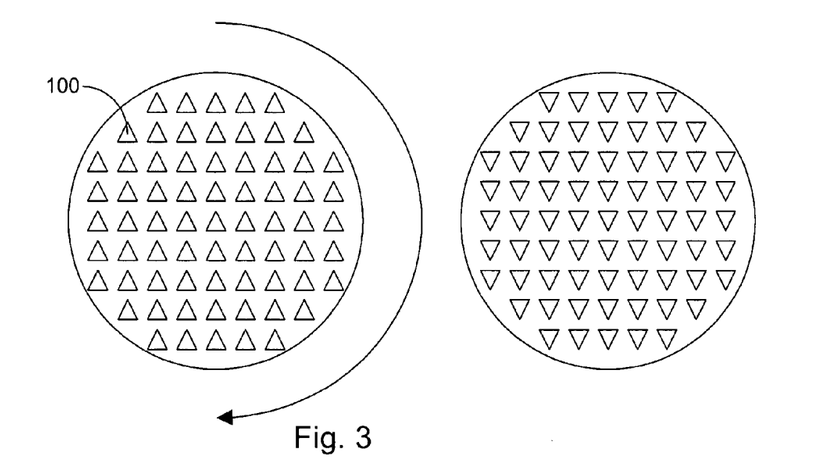
FIG. 3 illustrates rotation of a two dimensional angular scatter spectrum of radiation by 180°.

Then for each pixel 100 the value of intensity from the first measurement is subtracted from the value of intensity of the pixel in the corresponding position (after rotation) of the second measurement (or vice versa) and dividing each of the values for each pixel by 2. This eliminates TIS because the sensor asymmetry is invariant under wafer rotation. Overlay error is then determined from the results.

Unfortunately, this methodology reduces the throughput of substrates by 2 because TIS is usually process dependent and therefore this system should be used for each target on the substrate in case there are process variations across the substrate.

In an embodiment of the present invention, the following methodology is used.

The same two measurements of reflected and/or scattered radiation from a target portion (i.e. a grating) as described above are made, but over a longer integration time. The sensor asymmetry is calculated and stored on a pixel by pixel basis. This means that both of the intensity measurements at 0 and 180° substrate rotation is made at each pixel (which are at a plurality of pre-determined angular positions relative to the target pattern). That is, the sensor 18 is positioned stationary relative to the lens system 15 such that each pixel of the sensor 18 is positioned at a constant angle relative to the target pattern on the substrate W.

One of the two-dimensional angular scatter spectrums which are measured is rotated by 180° as described above with reference to FIG. 3. If there is no sensor asymmetry then that rotated two-dimensional angular scatter spectrum should be identical to the non-rotated angular scatter spectrum (which was measured at the other of 0 and 180° substrate rotation). Any sensor asymmetry will show up as a difference between the two images and an asymmetry correction value (or sensor correction value) for each pixel is calculated by subtracting the intensity of one of the two dimensional angular scatter spectrums (which should be the same were it not for asymmetry) from the other. This value is divided by 2 for each pixel.

These correction values can be used directly in correcting further measurements of target portions with 0° of substrate rotation. This is done by subtracting the asymmetry correction value for each pixel from the intensity value measured for the respective pixel.

In this embodiment, it is possible to save the asymmetry correction values for each of the pixels and apply those correction values to many measurements thereby hardly impacting on throughput. This is because the asymmetry correction value is substantially invariant with time.

Mathematically it does not matter in which order the calibration measurements and the actual measurements are taken but by doing the calibration measurements and the corresponding calculations first, the correction values can be subtracted from the overlay measurement image straight away and the uncorrected overlay image does not need to be stored and this may save storage space. The following analysis illustrates the above methodology in detail.

In order to correct for Tool Induced Shift (TIS), only 1 target is measured for 180° substrate rotation. This rotated measurement is used to calculate the sensor asymmetry and that can be used to correct the overlay measurements. In order to achieve sufficient signal-to-noise ratio, the measurement for the TIS correction is done with a long integration time (or averaging over multiple frames) e.g. sampling for over 400 milli seconds, or measuring 10 frames of 40 milli seconds each.

The substrate lot is then measured with 0° substrate rotation. The measured results are corrected using the calculated sensor asymmetry and then used to measure an overlay value in the normal way.

Analysis

Suppose we have 2 overlapping gratings with a small lateral shift x in the direction of the grating vector. This grating is measured for 0-degrees wafer rotation and in this case we write for the intensity in the $1^{st}$ and $-1^{st}$ diffraction order:

$$I_{1,0}=(I_0+\Delta I)(K_0+K_1 x)$$

$$I_{-1,0}=(I_0-\Delta I)(K_0-K_1 x)$$

Here, $K_0$ is the $1^{st}$ order diffraction efficiency at 0 shift, x is the shift between the overlapping gratings and $K_1$ is the sensitivity in the $1^{st}$ order diffraction efficiency to a shift x. The sensor asymmetry is represented by the term $\Delta I$ and $I_0$ is the average illumination intensity. In practice, all of these parameters with the exception of x depend on the position within the pupil plane. At 180° substrate rotation we can write for the measured intensities:

$$I_{1,\pi}=(I_0+\Delta I)(K_0-K_1 x)$$

$$I_{-1,\pi}=(I_0-\Delta I)(K_0+K_1 x)$$

We define asymmetry at 0 and 180° substrate rotation as:

$$A_0 = \frac{I_{1,0} - I_{-1,0}}{I_{1,0} + I_{-1,0}}$$

$$A_\pi = \frac{I_{1,\pi} - I_{-1,\pi}}{I_{1,\pi} + I_{-1,\pi}}$$

Inserting the expressions for the $1^{st}$ order intensities yields for the asymmetry:

$$A_0 = \frac{2I_0 K_1 x + 2K_0 \Delta I}{2I_0 K_0 + 2\Delta I K_1 x}$$

$$A_\pi = \frac{-2I_0 K_1 x + 2K_0 \Delta I}{2I_0 K_0 - 2\Delta I K_1 x}$$

We now define a normalized sensor asymmetry a and a normalized grating overlay sensitivity K as:

$$a = \frac{\Delta I}{I_0}$$

$$K = \frac{K_1}{K_0}$$

This yields the following simple expressions for the asymmetry at 0 and 180° substrate rotation:

$$A_0 = \frac{Kx + a}{1 + aKx}$$

$$A_\pi = \frac{-Kx + a}{1 - aKx}$$

These 2 concise expressions form the basis for the rest of the analysis. First, an expression will be derived for the overlay which includes the sensor asymmetry α and 2 measured asymmetries at only 0° substrate rotation. Secondly, it will be shown how we can measure this sensor asymmetry by measuring only 1 Overlay grating for 0 and 180° substrate rotation.

Overlay is measured by printing 2 grating pairs with a different (and preferably opposite) bias d that is superimposed on the unknown overlay error. So we measure an asymmetry for 2 different values of x:

$$x_1 = OV + d$$

$$x_2 = OV - d$$

This yields 2 measured asymmetries at 0° substrate rotation:

$$A_{0,1} = \frac{K(OV + d) + a}{1 + aK(OV + d)}$$

$$A_{0,2} = \frac{K(OV - d) + a}{1 + aK(OV - d)}$$

These 2 expressions are now rewritten as:

$$A_{0,1} + A_{0,1} aK(OV+d) = K(OV+d) + a$$

$$A_{0,2} + A_{0,2} aK(OV-d) = K(OV-d) + a$$

Subtracting and adding these 2 equations yields, respectively:

$$(A_{0,1} - A_{0,2}) + aK[OV(A_{0,1} - A_{0,2}) + d(A_{0,1} + A_{0,2})] = 2Kd \quad (1)$$

$$(A_{0,1}+A_{0,2})+aK[OV(A_{0,1}+A_{0,2})+d(A_{0,1}-A_{0,2})]=2KOV+2a \quad (2)$$

The measured asymmetries only occur as sums or differences so in order to simplify the expressions we define:

$$D=A_{0,1}-A_{0,2}$$

$$S=A_{0,1}+A_{0,2}$$

Using equation (1) we can write for K:

$$K = \frac{D}{2d - a(OVD + dS)} \quad (3)$$

Re-arranging the terms in equation (2) yields:

$$K[2OV-a(OVS+dD)]=S-2a \quad (4)$$

We need an expression for the overlay that is independent of the processing-dependent term K so we substitute equation (3) in equation (4) which yields:

$$\frac{D}{2d - a(OVD + dS)}[2OV - a(OVS + dD)] = S - 2a \quad (5)$$

Re-arranging this expression yields:

$$D[2OV-a(OVS+dD)]=(S-2a)[2d-a(OVD+dS)] \quad (6)$$

Using equation (6) we obtain the following expression for the overlay as a function of the measured asymmetries and the unknown yet constant sensor asymmetry:

$$OV = d\frac{S(1 + a^2) - 2a + 0.5a(D^2 - S^2)}{D(1 - a^2)} \quad (7)$$

For sufficiently small sensor asymmetry this expression can excellently be approximated by:

$$OV = d\frac{S - 2a}{D} \quad (8)$$

We select 1 overlay grating with an unknown (but sufficiently small) shift x between the 2 overlapping gratings. The asymmetry is measured for 0 and 180° substrate rotation. Adding and subtracting these asymmetries yields, respectively:

$$A_0 + A_\pi = 2a\frac{1 - (Kx)^2}{1 - (aKx)^2}$$

$$A_0 - A_\pi = 2Kx\frac{1 - a^2}{1 - (aKx)^2}$$

From these 2 equations, we can solve a and Kx exactly. In practice both terms are small ($\approx 0.2$) and we can ignore the term $(aKx)^2$.

$$A_0+A_\pi=2a(1-(Kx)^2)$$

$$A_0-A_\pi=2Kx(1-a^2)$$

This is still a rather nasty equation to solve. Since $\alpha$ and Kx are small, an iterative solution method can be used with a start value:

$$A_0+A_\pi=2a$$

$$A_0-A_\pi=2Kx$$

An example of this methodology is illustrated with reference to FIGS. 4-6.

Figure 4:
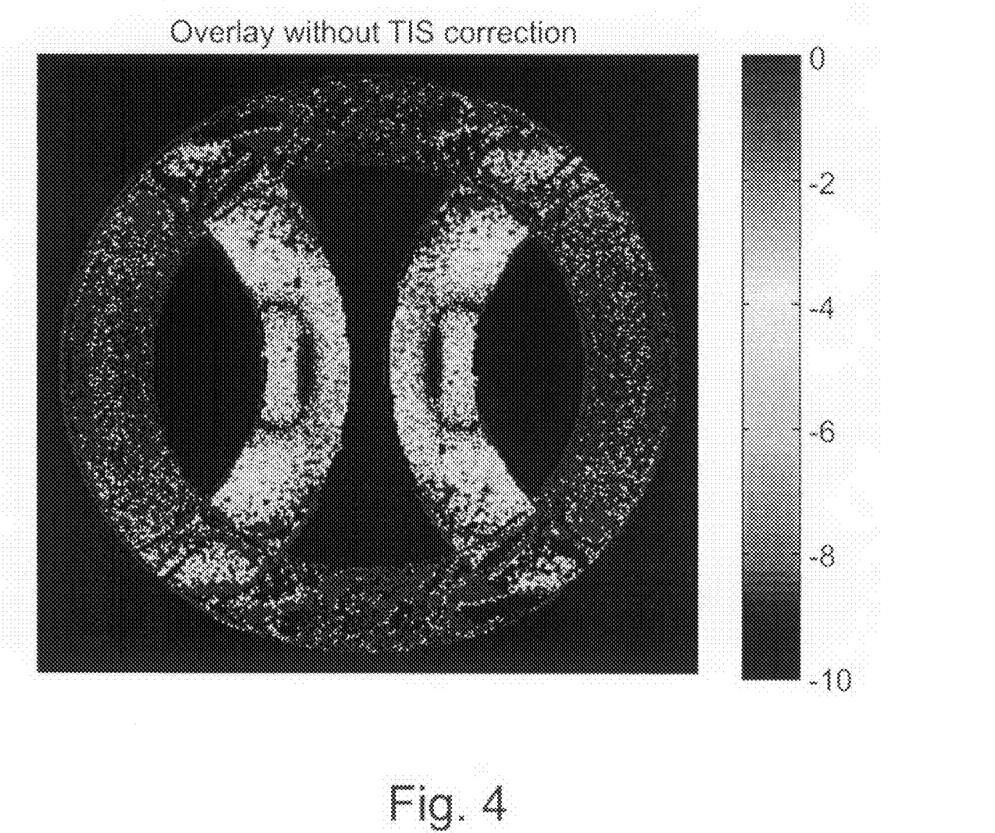
FIG. 4 depicts a two-dimensional angular scatter spectrum of radiation of an overlay measurement without TIS correction in accordance with an embodiment of the invention.

FIG. 4 shows raw measured overlay data obtained on a Copper Damascene wafer. Wavelength was 550 nm and the grating pitch was 500 nm. Annular illumination was used.

Figure 5:
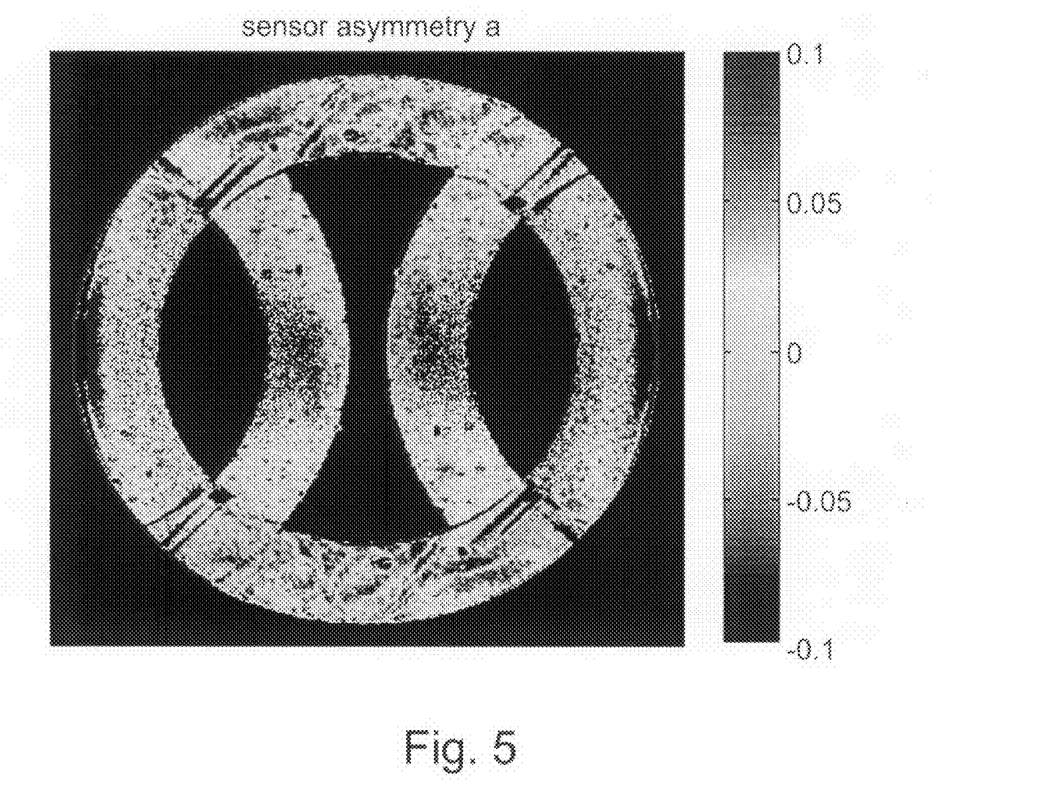
FIG. 5 depicts a map of asymmetry correction values in accordance with an embodiment of the invention.
Figure 6:
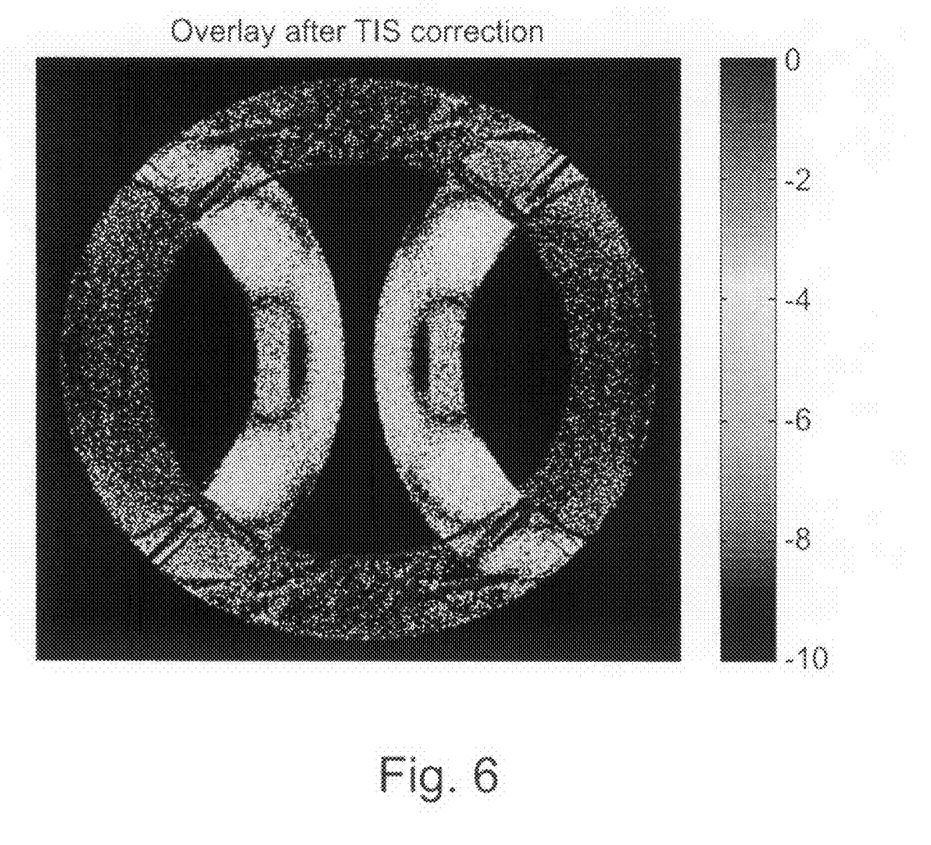
FIG. 6 depicts a two-dimensional angular scatter spectrum of radiation of an overlay measurement after TIS correction in accordance with an embodiment of the invention.

FIG. 5 shows an asymmetry correction map in which each of the pixels is assigned a correction value which has been calculated in accordance with the above mentioned method. FIG. 6 then shows the data of FIG. 4 to which the correction values of FIG. 5 have been applied. Grains due to illumination inhomogeneity are solved in accordance with an embodiment of this invention but large, very localized lines of excessive overlay errors due to zero overlay sensitivity or zero intensity cannot be corrected. Overlay errors due to zero sensitivity or zero intensity are fundamentally impossible to solve and are suppressed by suitable filtering during the post-processing operation. However, as can be seen from a comparison of FIGS. 4 and 6, an embodiment of the present invention effectively solves the grains due to illumination inhomogeneity.

In fact, scatterometry when used in measuring overlay often uses two different sources of illumination for separately measuring overlay in the x and y directions. In that case the different illumination sources have different polarization states (usually orthogonal). The calibrations described above can be repeated for each of the sources and the appropriate correction applied during measurement.

The above mentioned method can be used to correct for total asymmetries in the scatterometer. There are two sources of asymmetry in a scatterometer. These are the illumination branch and the high NA objective (that is microscope objective lens 15). From FIG. 2 it can be seen that there is a reference beam which passes through the half mirror 16 and is reflected by mirror 14 to the detector 18 without passing through the lens system 15 or going near the substrate W. The image of the relevance beam on the detector 18 is the same size and shape as the image of the pupil plane of the part of the illumination beam which is reflected and/or scattered by the substrate W. Normally this reference beam is used to normalize the reference image so as to eliminate the effects of source vibration.

In the present invention a similar process to that described above can be carried out on the reference beam thereby to produce an illumination beam asymmetry correction value for each pixel. Those can then be subtracted from the total asymmetry correction values (i.e. those obtained by the method described above) to determine the asymmetries in the lens system 15. Asymmetries in the lens system 15 are typically caused by dust and are generally relatively stable over a time whereas asymmetries in the illumination branch, which primarily derive from the laser, are quite variable. Thus, the asymmetries in the high NA objective can be stored and used for a significant period of time.

In an embodiment, the apparatus of FIG. 2 may also include a system to store the sensor correction value for each of the plurality of pre-determined angular positions. This system may include various types of memory.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A method of measuring asymmetry in a scatterometer, the method comprising:
   first illuminating a target pattern with radiation and measuring a first two-dimensional angular scatter spectrum of radiation reflected or scattered by the target pattern by using the scatterometer to measure intensity at a plurality of pre-determined angular positions relative to the target pattern;
   relatively rotating the target pattern and the scatterometer by about 180° in a plane substantially perpendicular to the optical axis of the scatterometer;
   second illuminating the target pattern with radiation and measuring a second two-dimensional angular scatter spectrum by using the scatterometer to measure intensity at the plurality of pre-determined positions relative to the target pattern and rotating the second angular scatter spectrum by about 180° to produce a third two-dimensional angular scatter spectrum; and
   producing a sensor correction value for each of the plurality of pre-determined angular positions by, for each of the plurality of pre-determined positions, subtracting the intensity at the respective pre-determined position of the first two-dimensional angular scatter spectrum from the intensity at the respective pre-determined position of the third two-dimensional angular scatter spectrum.

2. The method of claim 1, wherein each intensity at the pre-determined positions is measured over an integration time of at least about 200 milliseconds.

3. The method of claim 2, wherein each intensity at the pre-determined positions is measured over an integration time of at least about 400 milliseconds.

4. The method of claim 1, wherein the first illuminating, relatively rotating, second illuminating and producing are first carried out with radiation polarized in a first direction to obtain any asymmetry correction value for each of the plurality of pre-determined angular positions for radiation polarized in the first direction and then carried out with radiation polarized in a second direction to obtain a sensor correction value for each of the plurality of pre-determined angular positions for radiation polarized in the second direction.

5. The method of claim 1, further comprising updating the sensor correction value for each pixel by dividing it by two.

6. A method of measuring asymmetry in a scatterometer due to illumination beam asymmetry, the method comprising:
   first measuring with a detector of the scatterometer the intensity of radiation of an illumination beam at a plurality of pre-determined positions relative to the detector in a cross-section of the illumination beam to produce a first map of intensities;
   relatively rotating the illumination beam and the scatterometer by about 180° in a plane substantially perpendicular to an axis of the illumination beam;
   second measuring with the detector the intensity of radiation of the illumination beam at the plurality of pre-determined positions relative to the detector to produce a second map of intensities and rotating the second map of intensities by about 180° to produce a third map of intensities; and
   producing an illumination asymmetry correction value for each of the plurality of pre-determined positions by, for each of the plurality of pre-determined positions, subtracting the intensity at the respective pre-determined position of the first map of intensities from the intensity at the respective pre-determined position of the third map of intensities.

7. A method of measuring asymmetry in a scatterometer due to asymmetries in a microscope objective of the scatterometer, the method comprising:
   (1) obtaining sensor correction values using a method including
   first illuminating a target pattern with radiation and measuring a first two-dimensional angular scatter spectrum of radiation reflected or scattered by the target pattern by using the scatterometer to measure intensity at a plurality of pre-determined angular positions relative to the target pattern;
   relatively rotating the target pattern and the scatterometer by about 180° in a plane substantially perpendicular to an optical axis of the scatterometer;
   second illuminating the target pattern with radiation and measuring a second two-dimensional angular scatter spectrum by using the scatterometer to measure intensity at the plurality of pre-determined positions relative to the target pattern and rotating the second angular scatter spectrum by about 180° to produce a third two-dimensional angular scatter spectrum; and producing a sensor correction value for each of the plurality of pre-determined angular positions by, for each of the plurality of pre-determined positions, subtracting the intensity at the respective pre-determined position of the first two-dimensional angular scatter spectrum from the intensity at the respective pre-determined position of the third two-dimensional angular scatter spectrum; and (2) obtaining illumination asymmetry correction values using a method including first measuring with a detector of the scatterometer the intensity of radiation of an illumination beam at the plurality of pre-determined positions in a cross-section of the illumination beam to produce a first map of intensities;

relatively rotating the illumination beam and the scatterometer by about 180° in a plane substantially perpendicular to the axis of the illumination beam;

second measuring with the detector the intensity of radiation of the illumination beam at the plurality of pre-determined positions to produce a second map of intensities and rotating the second map of intensities by about 180° to produce a third map of intensities; and producing an illumination asymmetry correction value for each of the plurality of pre-determined positions by, for each of the plurality of pre-determined positions, subtracting the intensity at the respective pre-determined position of the first map of intensities from the intensity at the respective pre-determined position of the third map of intensities; and (3) for each pre-determined position, subtracting the respective illumination asymmetry correction value from the sensor correction value to obtain a microscope objective asymmetry value for each respective pre-determined position.

8. A method of measuring an overlay error in a substrate comprising:

projecting a beam of radiation onto a target pattern on the substrate;

measuring a first overlay two-dimensional angular scatter spectrum of radiation reflected or scattered by the target pattern by using a scatterometer to measure intensity at a plurality of pre-determined angular positions relative to the target pattern;

relatively rotating the target pattern and the scatterometer by about 180° in a plane substantially perpendicular to the optical axis of the scatterometer;

projecting a second beam of radiation onto the target pattern on the substrate and measuring a second two-dimensional angular scatter spectrum by using the scatterometer to measure intensity at the plurality of pre-determined positions relative to the target pattern;

rotating the second angular scatter spectrum by about 180° to produce a third two-dimensional angular scatter spectrum;

producing a sensor correction value for each of the plurality of pre-determined angular positions by, for each of the plurality of pre-determined positions, subtracting the intensity at the respective pre-determined position of the first two-dimensional angular scatter spectrum from the intensity at the respective pre-determined position of the third two-dimensional angular scatter spectrum;

computing a corrected two-dimensional angular scatter spectrum by subtracting, for each pre-determined position, the sensor correction value for each of the plurality of pre-determined angular positions from the measured intensity at the respective position of the overlay two-dimensional angular spectrum; and determining the overlay error from the corrected two-dimensional angular scatter spectrum.

9. A metrology apparatus configured to measure a property of a substrate, the apparatus comprising:

a radiation projector configured to illuminate a target pattern of a substrate with radiation;

a detector configured to measure an intensity of reflected or scattered radiation from the target pattern at a plurality of pre-determined angular positions relative to the target pattern;

a system configured to relatively rotate the target pattern and the scatterometer by about 180° in a plane substantially perpendicular to the target portion; and a controller adapted to control illumination of the target pattern with radiation, determine a first two-dimensional angular scatter spectrum of radiation reflected or scattered by the target pattern by using the detector to measure intensity at a plurality of pre-determined angular positions relative to the target pattern, relatively rotate the target pattern and the scatterometer by about 180° in a plane substantially perpendicular to an optical axis of the scatterometer, control illumination of the target pattern with radiation and determine a second two-dimensional angular scatter spectrum by using the detector to measure intensity at the plurality of pre-determined portions relative to the target pattern and rotate the second angular scatter spectrum by about 180° to produce a third two-dimensional angular scatter spectrum, and produce a sensor correction value for each of the plurality of pre-determined angular positions by, for each of the plurality of pre-determined positions, subtracting the intensity at the respective pre-determined position of the first two-dimensional angular scatter spectrum from the intensity at the respective pre-determined position of the third two-dimensional angular scatter spectrum.

10. The metrology apparatus of claim 9, further comprising a system to store the sensor correction value for each of the plurality of pre-determined angular positions.

11. The metrology apparatus of claim 9, wherein the controller is further adapted to project a beam of radiation onto a target pattern on a substrate;

measure an overlay two-dimensional angular scatter spectrum of radiation reflected or scattered by the target pattern by using the detector to measure intensity at the plurality of pre-determined angular positions relative to the target pattern, compute a corrected two-dimensional angular scatter spectrum by subtraction, for each pre-determined position, a respective the sensor correction value for a respective pre-determined position from the measured intensity at the respective position of the overlay two-dimensional angular spectrum, and determine the overlay error from the corrected two-dimensional angular scatter spectrum.

* * * * *